United States Patent
Radhakrishnan et al.

(10) Patent No.: US 6,639,072 B1
(45) Date of Patent: Oct. 28, 2003

(54) PROCESS FOR THE PREPARATION OF 6-(2,3-DICHLOROPHENYL)-1,2,4-TRIAZINE-3,5-DIAMINE, COMMONLY KNOWN AS LAMOTRIGINE

(75) Inventors: Tarur Venkatasubramanian Radhakrishnan, Maharashtra (IN); Thoovara Mohan Sasikumar, Maharashtra (IN); Anita Ranjan Srivastava, Maharashtra (IN)

(73) Assignee: RPG Life Sciences Limited, Maharashtra (IN)

( * ) Notice: Subject to any disclaimer, the term of this patent is extended or adjusted under 35 U.S.C. 154(b) by 0 days.

(21) Appl. No.: 10/149,429

(22) PCT Filed: Jan. 3, 2000

(86) PCT No.: PCT/IN00/00001

§ 371 (c)(1), (2), (4) Date: Jun. 24, 2002

(87) PCT Pub. No.: WO01/49669

PCT Pub. Date: Jul. 12, 2001

(51) Int. Cl.$^7$ .......... C07D 253/075
(52) U.S. Cl. ............ 544/182
(58) Field of Search ............ 544/182

(56) References Cited

U.S. PATENT DOCUMENTS

| | | | |
|---|---|---|---|
| 3,637,688 A | 1/1972 | Rees et al. | 544/182 |
| 4,486,354 A | 12/1984 | Baxter et al. | 544/182 |
| 4,602,017 A | 7/1986 | Sawyer et al. | 544/182 |
| 4,649,139 A | 3/1987 | Allan et al. | 544/182 |
| 4,847,249 A | 7/1989 | Sawyer et al. | 544/182 |
| 4,960,936 A | 10/1990 | Baumeister et al. | 544/182 |
| 5,912,345 A | 6/1999 | Winter et al. | 544/182 |
| 5,925,755 A | 7/1999 | Lee | 544/182 |
| 6,333,198 B1 | 12/2001 | Edmeades et al. | 544/182 |

FOREIGN PATENT DOCUMENTS

| | | |
|---|---|---|
| CA | 1119592 | 3/1982 |
| EP | 021121 | 1/1981 |
| EP | 059987 | 9/1982 |
| EP | 142306 | 5/1985 |
| EP | 247892 | 12/1987 |
| EP | 325892 | 8/1989 |
| EP | 963980 | 12/1999 |
| WO | 9620934 | 7/1996 |
| WO | 9620935 | 7/1996 |

*Primary Examiner*—John M. Ford
(74) *Attorney, Agent, or Firm*—Greenblum & Bernstein, P.L.C.

(57) ABSTRACT

A process for the preparation of 6-(2,3-dichlorophenyl)-1,2,4-triazine-3-5-diamine (lamotrigine) of the formula I:

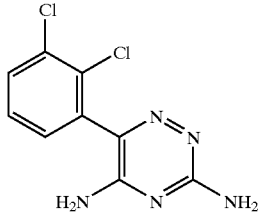

Formula I 2,3-Dichloronitrobenzene in $C_1$–$C_6$ aliphatic alkanol is hydrogenated at 55–90 psi gas pressure using metal catalyst at 27–35° C. 2,3-Dichloroaniline is diazotised and cyano-de-diazonised with metal cyanide at 65–80° C. 2,3-Dichlorobenzonitrile is hydrolysed and 2,3-dichlorobenzoic acid is chlorinated at 55–130° C. Cyano-de-halogenation of 2,3-dichlorobenzoyl chloride is carried out with a metal cyanide and alkali metal iodide by refluxing in an aprotic solvent under an inert atmosphere. 2,3-Dichlorobenzoyl cyanide is condensed with aminoguanidine bicarbonate in an organic solvent in acidic conditions using catalyst at 90–125° C. followed by insitu cyclisation of the Schiff's base by refluxing in an aliphatic alkanol with base. Crude lamotrigine is purified.

10 Claims, No Drawings

US 6,639,072 B1

PROCESS FOR THE PREPARATION OF 6-(2,3-DICHLOROPHENYL)-1,2,4-TRIAZINE-3,5-DIAMINE, COMMONLY KNOWN AS LAMOTRIGINE

TECHNICAL FIELD

This invention relates to a process for the preparation of 6-(2,3-dichlorophenyl)-1,2,4-triazine-3,5-diamine of the formula I:

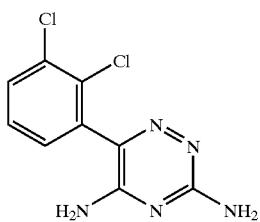

Formula I commonly known as Lamotrigine.

Lamotrigine, an anti-epileptic drug, elicits its action by suppressing seizures by inhibiting the release of excitatory neurotransmitters. Lamotrigine presently offers a worthwhile alternative for treating patients suffering from nitractable partial seizures coupled with or without secondary generalised seizures and therefore shows good potential for broader applications in other areas of epilepsy management.

BACKGROUND ART

One method of preparation of lamotrigine of the formula I involves reaction of 6-(2,3-dichlorophenyl)-5-chloro-3-thiomethyl 1,2,4-triazine of the formula II:

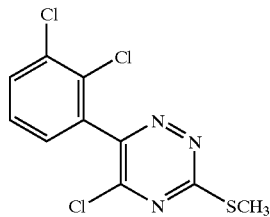

Formula II with ethanolic ammonia in a sealed tube at 180° C./250 psi pressure (PCT Publication No WO 96/20935). This process is time consuming (~72hours) and also produces lamotrigine in low yields because of which it is not commercially viable.

Another route for the synthesis of lamotrigine of the formula I involves photochemical reaction of the compound of the formula III:

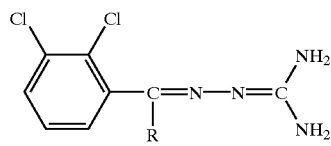

Formula III where R=CN or CONH$_2$, using ultraviolet or visible radiation in the presence of a base in an alkanol solvent and also heating when R=CN (PCT Publication No WO 96/20934). The preparation of the compound of the formula III involves expensive and hazardous reagents. Further, undesired by-products like the de-aminated hydroxy derivative of triazine formed during the photochemical reaction demand elaborate separation and purification techniques, thereby making this route lengthy and tedious, besides producing low yields of lamotrigine (<10%). Therefore this process is not Able for industrial scale manufacture of lamotrigine.

Yet another method for the synthesis of lamotrigine of the formula I involves cyclisation of the Schiff's base of the formula IV:

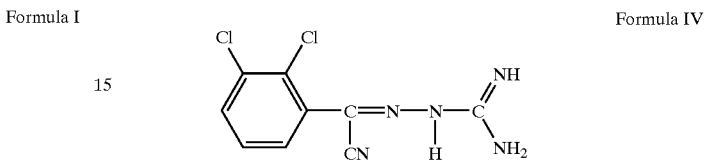

Formula IV by refluxing in C$_1$–C$_4$ aliphatic alkanol in the presence or absence of a strong base such as KOH (EP Patent No 21121 and U.S. Pat. Nos 4,602,017 and 4,847,249).

The Schiff's base of the formula IV may be prepared by a sequence of steps comprising:

(1) reaction of 2,3-dichloroiodobenzene of the formula V:

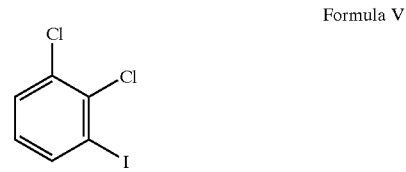

Formula V with magnesium, followed by reaction of the resulting Grignard moeity with solid carbondioxide;

(2) reaction of the resulting 2,3-dichlorobenzoic acid of the formula VI:

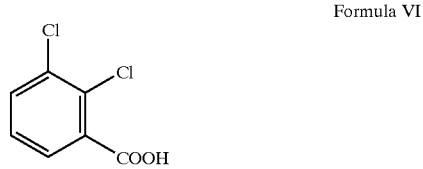

Formula VI with thionyl chloride in an inert atmosphere such as moisture free nitrogen gas;

(3) reaction of the resulting 2,3-dichlorobenzoyl chloride of the formula VII:

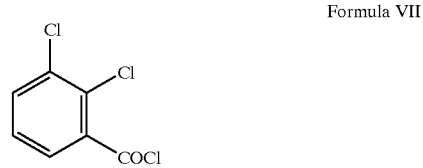

Formula VII with a metal cyanide and alkali metal iodide such as Cu(one)CN and KI in the presence of an organic solvent such as xylene in an inert atmosphere such as nitrogen; and (4) reaction of the resulting 2,3-dichlorobenzoylcyanide of the formula VIII:

Formula VIII with aminoguanidine bicarbonate in an organic solvent such as DMSO in aqueous acidic medium using 8N $HNO_3$. The purification of crude lamotrigine of the formula I thus obtained by cyclisation of the Schiff's base of the formula IV is carried out by recrystallisation from isopropanol (FP Patents Nos 59987 and 21121 and U.S. Pat. Nos 4,602,017 and 3,637,688).

The formation of 2,3-dichlorobenzoic acid of the formula VI for the preparation of the Schiff's base of the formula IV by the above route demands a dry environment thereby making the process laborious. These reactions leading to the Schiff's base of the formula IV also employ expensive and hazardous reagents like DMSO in large quantities and xylene. The conversion of 2,3-dichlorobenzoyl chloride to 2,3-dichlorobenzoyl cyanide takes 96 hours thereby making the entire process for the synthesis of the Schiff's base from 2,3-dichlorobenzoyl chloride time consuming (~7.5–10 days). This route also produces low yields of lamotrigine (~10%). Therefore this process for the preparation of lamotrigine is not feasible for industrial scale manufacture.

The Schiff's base of the formula IV may also be prepared by the reaction of 2,3-dichlorobenzoyl cyanide of the formula VIII with aminoguanidine bicarbonate in the presence of acetonitrile and dilute aqueous sulfuric acid (U.S. Pat. No 4,847,249). This route for the synthesis of the Schiff's base is reported to produce low yields of lamotrigine.

As lamotrigine has emerged to be one of the promising anti-epileptic and anti-convulsant for treating CNS disorders, its commercial production assumes significance. Despite the several routes known for the synthesis of lamotrigine there is still need for a route which is safe, convenient, efficient, economical and less time consuming.

DISCLOSURE OF THE INVENTION

An object of the invention is to provide a process for the preparation of 6-(2,3-dichlorophenyl)-1,2,4-triazine -3,5-diamine of the formula I, commonly known as lamotrigine, which is safe and convenient.

Another object of the invention is to provide a process for the preparation of 6-(2,3-dichlorophenyl)-1,2,4-triazine-3,5-diamine of the formula I, commonly known as lamotrigine, which is less time consuming.

Another object of the invention is to provide a process for the preparation of 6-(2,3-dichlorophenyl)-1,2,4-triazine -3,5-diamine of the formula I commonly known as lamotrigine, which is efficient and economical.

Another object of the invention is to provide a process for the preparation of 6-(2,3-dichlorophenyl)-1,2,4-triazine-3,5-diamine of the formula I, commonly known as lamotrigine, which is suitable for industrial scale manufacture.

According to the invention, there is provided a process for the preparation of 6-(2,3-dichlorophenyl)-1,2,4-triazine -3,5-diamine of the formula I:

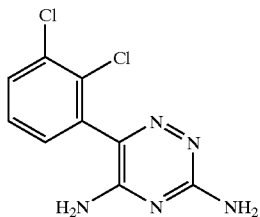

Formula I commonly known as lamotrigine which comprises:

a) reduction of 2,3-dichloronitrobenzene of the formula IX:

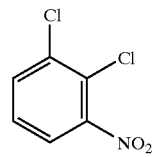

Formula IX in $C_1$–$C_6$ aliphatic alkanol with hydrogen gas at a pressure of 55–90 psi in the presence of a metal catalyst at 27–35° C.;

b) diazotisation of the resulting 2,3-dichloroaniline of the formula X:

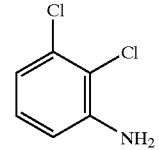

Formula X with sodium nitrite and a mineral acid at –5° to 5° C. followed by cyano-de-diazonation with a metal cyanide at 65–80° C.;

c) hydrolysis of the resulting 2,3-dichlorobenzonitrile of the formula XI:

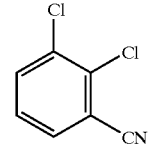

Formula XI under acidic or alkaline conditions;

d) chlorination of the resulting 2,3-dichlorobenzoic acid of the formula VI:

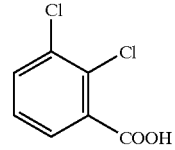

Formula VI with a chlorinating agent at 55–130° C.;

e) cyano-de-halogenation of the resulting 2,3-dichlorobenzoyl chloride of the formula VII:

Formula VII

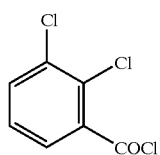

with a metal cyanide in the presence of an alkali metal iodide by refluxing in an aprotic solvent under an inert atmosphere;
f) condensation of the resulting 2,3-dichlorobenzoyl cyanide of the formula VIII:

Formula VIII

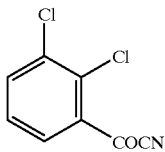

with aminoguanidine bicarbonate in an organic solvent in acidic conditions in the presence of a catalyst at 90°–125° C. followed by insitu cyclisation of the resulting Schiff's base of the formula IV:

Formula IV

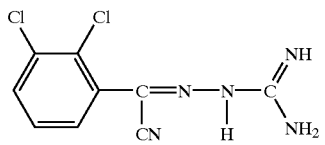

by refluxing in an aliphatic alkanol in the presence of a base; and
g) purification of the resulting crude lamotrigine of the formula I:

Formula I

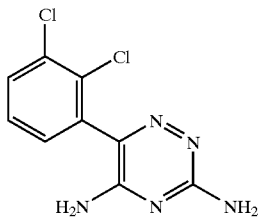

by a known method such as recrystallisation from an aliphatic alkanol or chromatographic separation The reduction of 2,3-dichloronitobenzene may be carried out by dissolution of 2,3-dichloronitrobenzene preferably in methanol. The pressure of the hydrogen gas for reduction may be preferably 50–70 psi, still preferably 80 psi and the temperature for the reduction may be preferably 30° C. The metal catalysts used in the reduction reaction may be nickel, Raney nickel platinum oxide, rhodium-platinum oxide, palladium-carbon, or palladium salts, preferably Raney nickel. An alkali or alkaline earth metal hydroxide such as NaOH, KOH, Ca(OH)$_2$ or Mg(OH)$_2$ may be optionally used in the reduction reaction.

For the diazotisation of 2,3-dichloroaniline, mineral acids such as HCl or H$_2$SO$_4$, preferably H$_2$SO$_4$, may be used. The diazotisation may be carried out preferably at 0° C. The excess sodium nitrite may be optionally decomposed using agents such as urea, sulfamic acid or a small amount of a primary amine dissolved in acid.

The cyano-de-diazonation reaction may be carried out using metal cyanides such as NaCN, KCN or Cu(one)CN or a mixture thereof. Preferably a mixture of Cu(one)CN and NaCN may be used. The cyano-de-diazonation may be carried out preferably at 65° C. Excess of cyanide may be optionally decomposed using sodium hypochlorite solution. A phase transfer catalyst such as crown ether or a quaternary ammonium salt in the presence of a nickel catalyst may be optionally used during the cyano-de-diazonation reaction.

The alkaline hydrolysis of 2,3-dichlorobenzonitrile may be carried out using NaOH or KOH in the presence of an aliphatic alkanol such as methanol or ethanol. Preferably methanolic NaOH at reflux temperatures may be used. The unreacted cyano compound may be extracted using toluene, ethyl acetate or a mixture of toluene and ethyl acetate, preferably toluene. Mineral acids such as H$_2$SO$_4$ or HCl may be used for acidic hydrolysis.

2,3-dichlorobenzoic acid may be chlorinated using SOCl$_2$ PCl$_3$ or PCl$_5$. Preferably SOCl$_2$ at 80° C. is used.

The cyano-de-halogenation reaction of 2,3-dichlorobenzoyl chloride is carried out under an inert atmosphere such as nitrogen atmosphere. The metal cyanide used may be Cu(one)CN, NaCN, KCN or a mixture of Cu(one) CN and NaCN. The alkali metal iodide may be NaI or KI. Preferably Cu(one)CN in the presence of KI may be used. The aprotic solvent for the reaction may be monochlorobenzene, xylene or any other aprotic solvent, preferably monochlorobenzene.

The condensation of 2,3-dichlorobenzoyl cyanide with aminoguanidine bicarbonate is carried out in the presence of a catalyst such as p-toluenesulfonic acid or a lewis acid catalyst such as AlCl$_3$, TiCl$_4$, FeCl$_3$, ZnCl$_2$, ZrCl$_4$ or any protonated acid such as HCl or H$_2$SO$_4$, in an organic solvent such as toluene or ethyl benzene, in acidic medium using HCl, HNO$_3$ or H$_2$SO$_4$. Preferably toluene and H$_2$SO$_4$ with p-toluenesulfonic acid at 100–120° C. may be used. Insitu cyclisation of the Schiff's base may be carried out in an aliphatic alkanol such as methanol with a strong base such as NaOH, KOH or NaOMe. Preferably methanol and NaOMe may be used.

For the recrystallisation of the crude lamotrigine, an aliphatic alkanol such as isopropanol ethanol or methanol, preferably methanol may be used.

Pharmaceutically acceptable acid addition salts of lamotrigine of the formula I may be prepared by treating lamotrigine of the formula I with acids such as hydrochloric, sulphuric, citric, tartaric, phosphoric, lactic, pyruvic, acetic, succinic, oxalic, fumaric, maleic, oxaloacetic, methane sulphonic, p-toluenesulphonic or benzenesulphonic acid.

According to the invention a new route is employed in the preparation of lamotrigine of the formula I. The substrate for the preparation thereof viz 2,3-dichloronitrobenzene and also the other reagents of the process of the invention are safe, inexpensive and easily available, thus eliminating the use of hazardous and expensive reagent reported in the prior art. The reactions leading to 2,3-dichlorobenzoic acid need not be carried out in a dry environment. Also chlorination of 2,3-dichloro-benzoic acid is conveniently carried out in a non-inert atmosphere without affecting the efficiency of the process. The use of catalyst during reduction of 2,3-dichloronitrobenzene at room temperature proceeds without dehalogenation thereby giving increased yield and purity of 2,3-dichloroaniline. Also the other intermediates of the process of the invention are obtained in good yields and purity. The conversion of 2,3-dichlorobenzoyl chloride to 2,3-dichlorobenzoyl cyanide requires about 6 hours, as against 96 hours reported in a process of the prior art.

Similarly the preparation of the Schiff's base from 2,3-dichlorobenzoyl chloride and further instiu cyclisation of the Schiff's base to lamotrigine also is less time consuming (8 hrs), as a 7.5–10 days reported in the prior art processes to prepare the Schiff's base itself. Therefore, the process of the invention is less time consuming and economical. The process of the invention gives a yield of 23% of lamotrigine (starting from 2,3-dichloronitrobenzene) as against a meagre yield of 10% (from 2,3-dichloroiodobenzene) reported in the prior art. Lamotrigine by our invention is also obtained with an excellent purity of 99.67%(by HPLC) after recrystallisation. The process of the invention is, therefore, efficient and economical and also suitable for industrial scale manufacture.

The following experimental example is illustrative of the invention but not limitative of the scope thereof.

EXAMPLE 1

Preparation of 2,3-dichloroaniline ($C_6H_3Cl_2NH_2$)

2,3-Dichloronitrobenzene (800 g, 4.17 moles) was dissolved in methanol (5.6 L) and charged into an autoclave. Raney nickel (80 g, 10% w/w) was added to the solution. The reaction mixture was hydrogenated at 80 psi for 3.5 hrs at 30° C. and filtered through celite. Methanol was distilled off to give 2,3-dichloroaniline ($C_6H_3Cl_2NH_2$).

| | |
|---|---|
| Yield = | 656 g |
| Purity = | 98% (when analysed by Gas Chromatography) |

Preparation of 2,3-dichlorobenzonitrile ($C_6H_3Cl_2CN$)

Conc. $H_2SO_4$ (1.365 L) and water (4.5 L) were charged into a suitable round bottom flak and the solution was cooled to 0° C. 2,3-Dichloroaniline (650 g, 4.012 moles) was added to the above solution and the reaction mixture was cooled and maintained at 0° C. A saturated solution of sodium nitrite (332.22 g, 4.815 moles) was added dropwise to the reaction while maintaining the temperature below 5° C. The reaction mixture was stirred at 0–5° C. for 1 hr and neutralised with sodium hydroxide at 0–5° C. The neutral solution was added dropwise to the cyanide solution [Cyanide solution obtained by mixing Cu(one)CN (365 g, 4.10 moles), NaCN (340 g 6.93 moles) and water (1.0 L)] at 65° C., under vigorous stirring for a period of 15 mins. The reaction mixture was warmed to 70° C. and stirred for another 15 mins. The 2,3-dichlorobenzonitrile so formed was extracted using ethylacetate (2.0 L). The organic layer was died over sodium sulfate and stripped to give a semi-solid mass of 2,3-dichlorobenzonitile ($C_6H_3Cl_2CN$).

| | |
|---|---|
| Yield = | 650 g |
| Purity = | 92% (when analysed by Gas Chromatography). |

Preparation of 2,3-dichlorobenzoic Acid ($C_6H_3Cl_2COOH$)

Sodium hydroxide (168.0 g, 4.2 moles, 1.2 eq) was dissolved in a mixture containing methanol (1.08 L) and water (600 ml) maintained at 5–10° C. This solution was then added to a flask containing 2,3-dichlorobenzonitrile (602.0 g, 3.5 moles). The reaction mixture was heated and refluxed for 10 hrs with slow stream of air bubbles being purged into the reaction mixture. Methanol was distilled off and water (1.0 L) was added to the reaction mixture. The reaction mixture was extracted with toluene (2×500 ml). The toluene fraction containing unreacted cyano compound was concentrated and recycled. The aqueous portion was treated with conc. HCl (32%/, 800 ml) to obtain a white solid preciptate of 2,3-dichlorobenzoic acid($C_6H_3Cl_2COOH$) which was filtered and dried.

| | |
|---|---|
| Yield = | 500 g |
| Purity = | 97% (when analysed by High Performance Liquid Chromatography) |

Preparation of 2,3-dichlorobenzoyl Chloride ($C_6H_3Cl_2COCl$)

2,3-Dichlorobenzoic acid (500 g, 2.618 moles) was charged into a 2 L four necked round bottom flask containing thionyl chloride (623 g, 5.235 moles) and heated at 80° C. for 1.0 hr to give 2,3-dichlorobenzoyl chloride ($C_6H_3Cl_2COCl$), after removal of excess of thionyl chloride.

| | |
|---|---|
| Yield = | 500 g |
| Purity = | 98% (when analysed by Gas Chromatography) |

Preparation of 2,3-dichlorobenzoyl Cyanide ($C_6H_3Cl_2COCN$)

Copper cyanide (215 g, 2.4 moles), potassium iodide (199 g, 1.2 moles) and monochlorobenzene (1.0 L) were added to a 3 L four necked round bottom flask containing 2,3-dichlorobenzoyl chloride (500g, 2.392 moles). The reaction mixture was heated to reflux under nitrogen blanket and maintained at 132-135° C. for 6 hrs. The reaction mixture was then filtered and monochlorobenzene distilled off to obtain 2,3-dichlorobenzoyl cyanide($C_6H_3Cl_6COCN$).

| | |
|---|---|
| Yield = | 470 g |
| Purity = | 97% (when analysed by Gas Chromatography) |

Preparation of 6-(2,3-dichlorophenyl)-1,2,4-triazine-3,5-diamine ($C_9H_7Cl_2N_5$)

Aminoguanidine bicarbonate (136 g, 1.0 mole) and toluene (1 L) were charged into a 3 L four necked round bottom flask. To this slurry was added conc sulfuric acid (98 g, 1.0 mole) in a slow stream and p-toluene sulfonic acid (25 g). The mixture was stirred for 15 mins and heated to 110° C. Water was azeotroped out from the mixture and the reaction mixture was cooled to 80° C. To this, 2,3-dichlorobenzoyl cyanide (100 g, 0.5 mole) was added the reaction mixture was refluxed for 3.5 hrs. Toluene was removed completely and the reaction mixture was cooled to 25° C. To it was added sodium methoxide (500 g) (solution methanol 25% w/w) and refluxed for 3 hrs. Methanol was removed completely and the reaction mixture was cooled to 20° C. Water (400 ml) was added to the reaction mixture and stirred at 20–25° C. for 1 hr. The precipitated solid was filtered and washed with water till free of base to give crude 6-2,3-dichlorophenyl)-1,2,4-triazine-3,5-diamine ($C_9H_7Cl_2N_5$).

| | |
|---|---|
| Yield = | 72 g |
| Purity = | 94% (when analysed by High Performance Liquid Chromatography) |

The crude product was recrystallised from methanol to give pure 6-(2,3-dichlorophenyl)-1,2,4triazine-3,5-diamine ($C_9H_7Cl_2N_5$).

| | |
|---|---|
| Yield = | 64 g |
| Purity = | 99.7% (when analysed by High Performance Liquid Chromatography). |

What is claimed is:

1. A process for the preparation of 6-(2,3-dichlorophenyl)-1,2,4-triazine -3,5-diamine of the formula I:

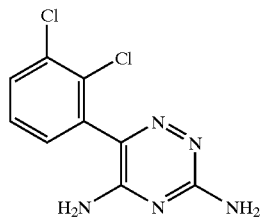

Formula I commonly known as lamotrigine which comprises:

a) reduction of 2,3-dichloronitrobenzene of the formula IX:

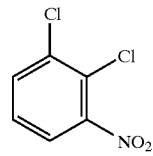

Formula IX in $C_1$–$C_6$ aliphatic alkanol with hydrogen gas at a pressure of 55–90 psi in the presence of a metal catalyst at 27–35° C.;

b) diazotisation of the resulting 2,3-dichloroaniline of the formula X:

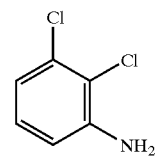

Formula X with sodium nitrite and a mineral acid at −5° to 5° C. followed by cyano-de-diazonation with a metal cyanide at 65–80° C.;

c) hydrolysis of the resulting 2,3-dichlorobenzonitrile of the formula XI:

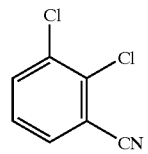

Formula XI under acidic or alkaline conditions;

d) chlorination of the resulting 2,3-dichlorobenzoic acid of the formula VI:

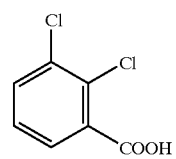

Formula VI with a chlorinating agent at 55–130° C.;

e) cyano-de-halogenation of the resulting 2,3-dichloro-benzoyl chloride of the formula VII:

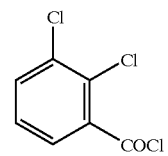

Formula VII with a metal cyanide in the presence of an alkali metal iodide by refluxing in an aprotic solvent under an inert atmosphere;

f) condensation of the resulting 2,3-dichlorobenzoyl cyanide of the formula VIII:

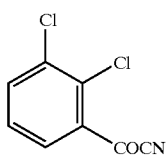

Formula VIII with aminoguanidine bicarbonate in an organic solvent in acidic conditions in the presence of a catalyst at 90–125° C. followed by insitu cyclisation of the resulting Schiff's base of the formula IV:

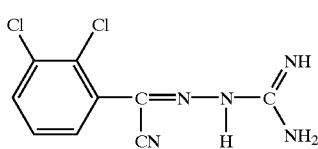

Formula IV by refluxing in an aliphatic alkanol in the presence of a base; and g) purification of the resulting crude lamotrigine of the formula I:

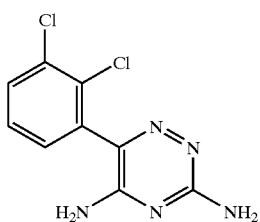

Formula I by a known method such as recrystallisation from an aliphatic alkanol or chromatographic separation.

2. A process as claimed in claim 1, wherein the reduction of 2,3-dichloronitrobenzene is carried out in methanol using hydrogen gas at a pressure of 80 psi in the presence of Raney nickel at 30° C.

3. A process as claimed in claim 1, wherein the diazotisation of 2,3-dichloroaniline is carried out using sodium nitrite and $H_2SO_4$ at 0° C.

4. A process as claimed in claim 1, wherein the cyano-de-diazonation is carried out using a mixture of Cu(one)CN and NaCN at 65° C.

5. A process as claimed in claim 1, wherein the hydrolysis of 2,3-dichlorobenzonitrile is carried out by refluxing with methanolic NaOH.

6. A process as claimed in claim 1, wherein chlorination of 2,3-dichlorobenzoic acid is carried out with $SOCl_2$ at 80° C.

7. A process as claimed in claim 1, wherein the cyano-de-halogenation of 2,3-dichlorobenzoyl chloride is carried out with Cu(one)CN and KI in monochlorobenzene under nitrogen atmosphere at 132–135° C.

8. A process as claimed in claim 1, wherein 2,3-dichlorobenzoyl cyanide is condensed with aminoguanidine bicarbonate in toluene in the presence of sulphuric acid and p-toluene sulfonic acid at 100–120° C.

9. A process as claimed in claim 1, wherein insitu cyclisation of the schiff's base is carried out in methanol in the presence of NaOMe.

10. A process as claimed in claim 1, wherein crude lamotrigine is purified by recrystallisation from methanol.

* * * * *